US008183026B2

(12) United States Patent
Lawrence et al.

(10) Patent No.: US 8,183,026 B2
(45) Date of Patent: May 22, 2012

(54) METHODS OF PREPARATION OF LIVE ATTENUATED BACTERIAL VACCINE BY ALTERATION OF DNA ADENINE METHYLASE (DAM) ACTIVITY IN THOSE BACTERIA (75) Inventors: Mark L. Lawrence, Starkville, MS (US); Daniel B. Paulsen, Baton Rouge, LA (US); Daniel W. Scruggs, Starkville, MS (US)

(73) Assignee: Mississippi State University, Mississippi State, MS (US)

(*) Notice: Subject to any disclaimer, the term of this patent is extended or adjusted under 35 U.S.C. 154(b) by 507 days.

(21) Appl. No.: 10/541,246

(22) PCT Filed: Jan. 14, 2004

(86) PCT No.: PCT/US2004/000740
§ 371 (c)(1),
(2), (4) Date: Sep. 12, 2006

(87) PCT Pub. No.: WO2004/064776
PCT Pub. Date: Aug. 5, 2004

(65) Prior Publication Data
US 2007/0082009 A1    Apr. 12, 2007

Related U.S. Application Data (60) Provisional application No. 60/439,796, filed on Jan. 14, 2003, provisional application No. 60/439,790, filed on Jan. 14, 2003.

(51) Int. Cl.
*A01N 63/00* (2006.01)
*C12N 1/00* (2006.01)
*C12N 1/12* (2006.01)
*C12N 1/36* (2006.01)

(52) U.S. Cl. ............... 435/243; 435/245; 435/252.1; 424/93.1; 424/93.4

(58) Field of Classification Search ................ None
See application file for complete search history.

(56) References Cited

U.S. PATENT DOCUMENTS

| 4,798,791 | A | * | 1/1989 | Anderson et al. | ............ 435/69.1 |
| 5,403,863 | A | | 4/1995 | Hayes et al. | |
| 7,026,155 | B2 | * | 4/2006 | Mahan et al. | ............ 435/252.1 |
| 2002/0068068 | A1 | | 6/2002 | Mahan et al. | |

OTHER PUBLICATIONS

U.S. Appl. No. 10/767,441, filed Jan. 30, 2004, Pending.
U.S. Appl. No. 11/372,187, filed Mar. 10, 2006, Pending.
Carter, "Observations on the Pathology and Bacteriology of Shipping Fever in Canada", Can. J. Comp. Med., vol. 18, No. 10, pp. 359-364, 1954.
Collier, "Significance of Bacteria in Bovine Respiratory Disease", A.V.M.A., vol. 153, No. 12, pp. 1645-1651, 1968.
Schiefer, et al., "Correlation of Microbiological and Histological Findings in Bovine Fibrinous Pneumonia", Vet. Pathol., vol. 15, pp. 313-321, 1978.
Purdy, et al., "Serotyping and Enzyme Characterization of *Pasteurella haemolytica* and *Pasteurella multocida* Isolates Recovered from Pneumonic Lungs of Stressed Feeder Calves", Current Microbiology, vol. 34, pp. 244-249, 1997.
Allen, et al., "The Microbial Flora of the Respiratory Tract in Feedlot Calves: Associations between Nasopharyngeal and Bronchoalveolar Lavage Cultures", Can. J. Vet. Res., vol. 55, pp. 341-346, 1991.
Singer, et al., "Assessment of spatial and temporal clustering of ampicillin- and tetracycline-resistant strains of *Pasteurella multocida* and *P haemolytica* isolated from cattle in California", JAVMA, vol. 212, No. 7, pp. 1001-1005, 1998.
Gourlay, et al., "Experimental *Pasteurella multocida* pneumonia in calves", Res. Vet. Sci., vol. 47, pp. 185-189, 1989.
Bryson, et al., "Observations on outbreaks of respiratory disease in housed calves—(1) Epidemiological, clinical and microbiological findings", Vet. Rec., vol. 103, pp. 485-489, 1978.
Virtala, et al., "Epidemiologic and pathologic characteristics of respiratory tract disease in dairy heifers during the first three months of life", JAVMA, vol. 208, No. 12, pp. 2035-2042, 1996.
Boyce, et al., "The Capsule is a Virulence Determinant in the Pathogenesis of *Pasteurella multocida* M1404 (B:2)", Infection and Immunity, vol. 68, No. 6, pp. 3463-3468, 2000.
Rimler, et al., "Lipopolysaccharides of the Heddleston serotypes of *Pasteurella multocida*", Am. J. Vet. Res., vol. 45, No. 4, pp. 759-763, 1984.
Brogden, et al., "Incubation of *Pasteurella haemolytica* and *Pasteurella multocida* lipopolysaccharide with sheep lung surfactant", Am. J. Vet. Res., vol. 47, No. 4, pp. 727-729, 1986.
Confer, et al., "Intranasal vaccination of rabbits with *Pasteurella multocida* A:3 outer membranes that express iron-regulated proteins", AJVR, vol. 62, No. 5, pp. 697-703, 2001.
Geschwend, et al., "Untersuchungen zu den Proteinen de auBeren Membran von Pasteurellen 2. Mittelilung; Eisenregulierte Proteine der auBeren Membran bei *Pasteurella multocida* und *Pasteurella haemolytica*", Berl. Munch Tierarztl Wschr, vol. 110, p. 386-390, 1997.
Negrete-Abascal, et al., "Secretion of Proteases from *Pasteurella multocida* Isolates", Curr. Micribiol., vol. 38, pp. 64-67, 1999.
Straus, et al., "In Vivo Production of Neuraminidase by *Pasteurella haemolytica* in Market Stressed Cattle After Natural Infection", Current Microbiol., vol. 37, pp. 240-244, 1998.
White, et al., "Extracellular Neuraminidase Production by a *Pasteurella multocida* A:3 Strain Associated with Bovine Pneumonia", Infection and Immunity, vol. 63, No. 5, pp. 1703-1709, 1995.

(Continued)

*Primary Examiner* — Albert Navarro
(74) *Attorney, Agent, or Firm* — Butler, Snow, O'Mara, Stevens & Cannada PLLC (57) ABSTRACT

Live attenuated bacteria vaccines are provided. Also provided are methods by which such vaccines can be obtained, including: a method by which a copy of the dam gene from a pathogenic bacteria is cloned into a plasmid capable of replication in the same bacteria species such that it is overexpressed from either a lac promoter, tac promoter, araBAD promoter, trc promoter, trp promoter, T7, SP6, or T5 bacteriophage promoters, a native promoter from that species, or other appropriate promoter. The plasmid containing the dam gene is then transferred into the pathogens to cause increased expression of Dam resulting in the formation of a live attenuated bacterial vaccines. Alternative methods for producing the vaccine are also provided including altering or replacing the chromosomal promoter for the native dam gene so as to alter Dam expression or mutating or replacing the native dam gene so as to alter the expression of Dam in a pathogenic bacteria.

21 Claims, 2 Drawing Sheets

OTHER PUBLICATIONS

Galdiero, et al., "Effects of the major *Pasteurella multocida* porin on bovine neutrophils", AJVR, vol. 59, No. 10, pp. 1270-1274, 1998.

Fuller, et al., "Identification of *Pasteurella multocida* virulence genes in a septicemic mouse model using signature-tagged mutagenesis", Microb. Pathog., vol. 29, pp. 25-38, 2000.

May, et al., "Complete genomic sequence of *Pasteurella multocida*, Pm70", Proc. Natl. Acad. Sci. USA, vol. 98, No. 6, pp. 3460-3465, 2001.

Blyn, et al., "Regulation of *pap* pilin phase variation by a mechanism involving differential Dam methylation states", The EMBO J., vol. 9, No. 12, pp. 4045-4054, 1990.

Braaten, et al., "Methylation Patterns in *pap* Regulatory DNA Control Pyelonephritis-Associated Pili Phase Variation in *E. coli*", Cell, vol. 76, pp. 577-588, 1994.

van der Woude, et al., "Leucine-responsive regulatory protein and deoxyadenosine methylase control the phase variation and expression of the *sfa* and *daa* pili operons in *Escherichida coli*", Mol. Microbiol., vol. 11, No. 4, pp. 605-618, 1994.

Henderson, et al., "The Major Phase-Variable Outer Membrane Protein of *Escherichia coli* Structurally Resembles the Immunoglobulin A1 Protease Class of Exported Protein and is Regulated by a Novel Mechanism Involving Dam and OxyR", J. of Bacteriol., vol. 181, No. 7, pp. 2132-2141, 1999.

Heithoff, et al., "An Essential Role for DNA Adenine Methylation in Bacterial Virulence", Science, vol. 284, pp. 967-970, 1999.

Julio, et al., "DNA Adenine Methylase is Essential for Viability and Plays a Role in the Pathogenesis of *Yersinia pseudotuberculosis* and *Vibrio cholerae*", Infect. and Immun., vol. 69, No. 12, pp. 7610-7615, 2001.

Fleischmann, et al., "Whole-Genome Random Sequencing and Assembly of *Haemophilus influenza* Rd", Science, vol. 269, pp. 496-512, 1995.

Palmer, et al., "The *dam* and *dcm* strains of *Escherichida coli*—a review", Gene, vol. 143, Supplement 37, pp. 1-12, 1994.

Ausubel, et al., "Preparation of Genomic DNA from Bacteria", Current Protocols in Molecular Biology, New York, New York: John Wiley and Sons, 1994.

Altschul, et al., "Gapped BLAST and PSI-BLAST: a new generation of protein database search programs", Nucleic Acids Research, vol. 25, No. 17, pp. 3389-3402, 1997.

Thompson, et al., "CLUSTAL W: improving the sensitivity of progressive multiple sequence alignment through sequence weighting, position-specific gap penalties and weight matrix choice", Nucleic Acids Res., vol. 22, No. 22, pp. 4673-4680, 1994.

Reese, et al., "Large Scale Sequencing Specific Neural Networks for Promoter and Splice Site Recognition", Biocomputing: Proceedings of 1996 Pacific Symposium, pp. 737-739, 1996.

Willson, et al., "Characterization of a Multiple Antibiotic Resistance Plasmid from *Haemophilus ducreyi*", Antimicrob. Agents Chemother., vol. 33, No. 9, pp. 1627-1630, 1989.

Jablonski, et al., "Conditions for transformation of *Pasteurella multocida* by electroporation", Micro. Pathog., vol. 12, pp. 63-68, 1992.

Jonczyk, et al., "The *Escherichia coli dam* gene is expressed as a distal gene of a new operon", Mol. Gen. Genet., vol. 217, pp. 85-96, 1989.

Herman, et al., "*Escherichia coli* K-12 Clones That Overproduce *dam* Methylase Are Hypermutable", J. Bacteriol., vol. 145, pp. 644-646, 1981.

Glickman, et al., "Induced Mutagenesis in *dam*—Mutants of *Escherichia coli*: A Role for 6-Methyladenine Residues in Mutation Avoidance", Mol. Gen. Genet., vol. 163, pp. 307-312, 1978.

Bale, et al., "Characterization of DNA Adenine Methylation Mutants of *Escherichia coli* K12", Mutant. Res., vol. 59, pp. 157-165, 1979.

Marinus, et al., "Biological Functions for 6-Methyladenine Residues in the DNA of *Escherichia coli* K12", J. Mol. Biol., vol. 85, pp. 309-322, 1974.

Geier, et al., "Recognition Sequence of the *dam* Methylase of *Escherichia coli* K12 and Mode of Cleavage of *Dpn* I Endonuclease", J. Biol. Chem., vol. 254, No. 4, pp. 1408-1413, 1979.

Modrich, "Methyl-directed DNA Mismatch Correction", J. Biol. Chem., vol. 264, No. 12, pp. 6597-6600, 1989.

Marinus, et al., "Correlation of DNA adenine methylase activity with spontaneous mutability in *Escherichia coli* K-12", Gene, vol. 28, pp. 123-125, 1984.

Heithoff, et al., "*Salmonella* DNA Adenine Methylase Mutants Confer Cross-Protective Immunity", Infect. and Immun., vol. 69, No. 11, pp. 6725-6730, 2001.

Confer, et al., "Antibody responses of cattle to outer membrane proteins of *Pasteurella multocida* A:3", Am. J. Vet. Res., vol. 57, No. 10, pp. 1453-1457, 1996.

Adler, et al., "Candidate vaccine antigens and genes in *Pasteurella multocida*", J. of Biotechnol., vol. 73, pp. 83-90, 1999.

Cardella, et al., "Vaccination Studies Against Experimental Bovine *Pasteurella* Pneumonia", Can. J. Vet. Res., vol. 51, pp. 204-211, 1987.

Panciera, et al., "Bovine pneumonic pasteurellosis: Effect of vaccination with live *Pasteurella* species", Am. J. Vet. Res., vol. 45, No. 12, pp. 2538-2542, 1984.

Chengappa, et al., "Efficacy of a Live *Pasteurella multocida* Vaccine for the Prevention of Experimentally Induced Bovine Pneumonic Pasteurellosis", Vet. Microbiol., vol. 21, pp. 147-154, 1989.

Paustian, et al., "*Pasturella multocida* Gene Expression in Response to Iron Limitation", Infect. and Immun., vol. 69, No. 6, pp. 4109-4115.

* cited by examiner

FIGURE 1

FIGURE 2

SEQUENCE LISTING

```
<160> NUMBER OF SEQ ID NOS: 7

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gggcgctgga gcagtatt                                                        18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgtagcggag cataaggt                                                        18
```

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgaggaaacg gtctggtttc tc                                           22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctggaaaat tgcgtctcgt c                                            21

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggatcctgcg ttatcccc                                                18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tctagatgtt gccaatgc                                                18

<210> SEQ ID NO 7
<211> LENGTH: 35
<212> TYPE: DNA
<213> ORGANISM: Pasteurella multocida
<220> FEATURE:
<221> NAME/KEY: modified_base
<222> LOCATION: (7)..(23)
<223> OTHER INFORMATION: a, c, g, t, unknown or other
<220> FEATURE:
<221> NAME/KEY: modified_base
<222> LOCATION: (30)..(34)
<223> OTHER INFORMATION: a, c, g, t, unknown or other

<400> SEQUENCE: 7
tggaaannnn nnnnnnnnnn nnntagcgtn nnnng                             35

METHODS OF PREPARATION OF LIVE ATTENUATED BACTERIAL VACCINE BY ALTERATION OF DNA ADENINE METHYLASE (DAM) ACTIVITY IN THOSE BACTERIA

CROSS-REFERENCE TO RELATED APPLICATIONS

This application is the entry into the U.S. National Stage of PCT Application No. PCT/US04/00740 filed 14 Jan. 2004, and claims priority from U.S. Provisional Patent Application Ser. No. 60/439,796, filed Jan. 14, 2003 and U.S. Provisional Patent Application Ser. No. 60/439,790, filed Jan. 14, 2003, the disclosures of which are hereby incorporated by reference.

This invention was made with Government support under Grant No. MISVO81310 awarded by the U.S. Department of Agriculture-CSREES. The Government may have certain rights in this invention.

BACKGROUND OF THE INVENTION

1. Field of the Invention

The present invention relates to methods of preparation of avirulent live bacterial vaccines. Particularly, the present invention relates to attenuated live bacterial vaccines of the Pasteurellaceae family. More particularly, the invention is directed to methods of manufacturing live attenuated bacterial vaccines by the alteration of DNA adenine methylase (Dam) expression in the veterinary pathogens *Pasteurella multocida, Mannheimia haemolytica, Actinobacillus pleuropneumoniae, Haemophilus somnus, Actinobacillus suis*, and *Haemophilus parasuis*. More particularly, the inventors have discovered methods of manufacturing live attenuated bacterial vaccines wherein the alteration of DNA adenine methylase (Dam) expression in selected pathogens can be accomplished, for example, by 1) placing the Pasteurellaceae dam gene on a plasmid under the control of a promoter that causes increased dam expression in the particular bacteria species and results in live attenuated bacterial vaccines, 2) altering the chromosomal promoter for the dam gene so as to alter the expression of Dam in any of the above listed pathogenic bacteria, or 3) mutation of the dam gene so as to alter the expression of Dam in any of the above listed pathogenic bacteria. By altering Dam expression the bacteria is attenuated and suitable for use in live attenuated bacterial vaccines.

2. Background of the Technology

Livestock production is a major part of the world's agriculture economy. Disease annually depletes livestock populations and increases production costs. Either by prevention or post-infection treatment, the goal of limiting the impact of disease on livestock production is of great economic importance. Prior to the introduction of antibiotics, the practice of culling diseased animals and destroying them to prevent the spread of disease was, in many cases the only option open to the livestock producer.

During the past half century, the use of antibiotics has become vital for the treatment of bacterial infections in the livestock industry. The emergence of antibiotic resistance as a serious problem in human medicine has prompted concern about the public health implications of antibiotic use in agriculture. Antibiotics have been used in farm animals for three main reasons: 1) therapy to treat an identified illness, 2) prophylaxis to prevent disease in animals, and 3) performance enhancement to increase feed conversion, animal growth rate, or yield per animal.

Prevention of disease is always preferable to treatment of disease because treatments can be ineffective, costly, and due to the possibility of antibiotic resistance potentially unhealthful for consumers. The use of antibiotics as a preventive measure can also include the undesirable overuse of antibiotics.

Immunization of livestock against the effect of infectious diseases can be more effective than attempts to protect livestock with nonspecific antibiotic treatments. Conventional methods of immunization require the preparation of a vaccine using killed or weakened infectious organisms or agents. All too frequently, immunization failures in livestock might be attributed to one or more failures in the immunization process. The chemical or physical manipulations required for production of killed bacterial vaccines may alter the effectiveness of the immune response, causing vaccine failure. The immune response is very specific and the vaccine may contain organisms of the same family as the target disease, but if they are not of the same serotype (type within the family), the results may be disappointing. Vaccines can also lack the necessary potency or purity needed to properly stimulate an immune response in the vaccinated animal. Other problems commonly encountered in the vaccination of livestock may be outdated vaccine, improper handling or mixing of vaccines, or other delivery failures. For a variety of reasons, conventional vaccination of livestock can sometimes have disappointing results. For this reason, many livestock producers continue to rely on antibiotics as an infectious disease preventive measure.

There exists therefore a need to provide an effective method of preventing disease in livestock without the potential health hazard that can be associated with the prophylactic use of antibiotics in otherwise healthy livestock. Effective vaccines would be more economical and would avoid the potential for unnecessary antibiotic usage.

The concept of the present invention includes the preparation of attenuated live bacterial vaccines for a wide variety of pathogenic bacteria. Of particular interest to the inventors are the livestock diseases caused by veterinary pathogens *Pasteurella multocida, Mannheimia haemolytica, Actinobacillus pleuropneumoniae, Haemophilus somnus, Actinobacillus suis*, and *Haemophilus parasuis*.

The association of *Pasteurella multocida* with bovine respiratory disease (BRD) has been well known since the early 1950's[1]. In most survey studies of feedlot BRD, *Mannheimia (Pasteurella) haemolytica* has been the most commonly isolated species, followed closely by *Pasteurella multocida*, with fewer cases of *Haemophilus somnus*[2-4]. However, in some studies, *P. multocida* is the most common isolate[5,6], and many BRD investigators have become convinced that *P. multocida* is an important primary pathogen in BRD[4,7]. In young dairy calves, *P. multocida* is the most frequently isolated species from cases of pneumonia[8,9]. *P. multocida* is a commensal occupant of the upper respiratory tract of cattle[5]; the induction of disease is often associated with stress, especially from transportation. Potential virulence factors include polysaccharide capsule[10], lipopolysaccharide,[11,12] iron-regulated outer membrane proteins[13,14], proteases[15,16], neuraminidase[16,17], and porins[17,18]. Recently, signature tagged mutagenesis was employed to identify 25 genes that, when inactivated, reduce virulence in the mouse intraperitoneal model[19]. The predicted gene products fell into 4 categories: regulatory, biosynthetic, known virulence factors, and unknown or novel. The whole genome sequence of an avian *P. multocida* isolate was published in 2001[20], which allowed identification of 104 potential virulence-related genes. However, the mechanisms that control expression of these potential virulence factors have not been determined.

DNA adenine methylase (Dam) is an important virulence gene regulator in the Enterobacteriaceae. In E. coli, Dam regulates transcription of several pili operons, including the pap (pyelonephritis-associated pili)[21,22], sfa (S pili), fae (K88 pili), and daa (F1845 pili) operons[23], and it regulates expression of a major outer membrane protein (Ag43)[24]. A Salmonella enterica serovar Typhimurium dam mutant strain had altered expression of more than 20 in vivo-induced (ivi) genes (elevated by 2- to 18-fold in a dam inactivated mutant compared to a wild type dam positive strain)[25].

In bacterial species that possess a dam gene, alteration of dam expression causes substantial attenuation, as well as enhanced, protective antigenicity [25]. A S. enterica serovar Typhimurium dam mutant had a $LD_{50}$ that was >10$^4$ higher than wild type parent strain, and it was effective as a live attenuated vaccine after a single oral dose[25]. An overexpressing dam strain was also highly attenuated in mice [25]. In Yersinia pseudotuberculosis and Vibrio cholerae, inactivation of the dam gene was shown to be a lethal mutation[26]. However, plasmid-mediated overexpression of the dam gene in Y. pseudotuberculosis resulted in a >6000-fold increase in $LD_{50}$ in mice compared to wild type and a 5-fold defect in colonization of *V. cholerae* in a suckling mouse model compared to wild type[26].

Although dam genes have been identified in the Pasteurellaceae as a result of genome sequencing projects[20,27], there have been no reports of functional characterization of dam in any of these species.

SUMMARY OF THE INVENTION

This invention involves the preparation of avirulent live bacteria vaccines. The inventors have discovered methods of manufacturing live attenuated bacterial vaccines by the alteration of DNA adenine methylase (Dam) expression in pathogenic bacteria. Exemplary of the present invention, the inventors have discovered a method of preparation of attenuated live bacteria vaccines for the Pasteurellaceae family and more particularly for the veterinary pathogens *Pasteurella multocida, Mannheimia haemolytica, Actinobacillus pleuropneumoniae, Haemophilus somnus, Actinobacillus suis*, and *Haemophilus parasuis*.

One embodiment of the present invention provides a method of preparation of attenuated live bacteria vaccines that includes, for example, placing the Pasteurellaceae dam gene on a plasmid under the control of a promoter that causes increased dam expression in the particular bacteria species and results in effective live attenuated bacterial vaccines. Another embodiment of the present invention provides a method of preparation of attenuated live bacteria vaccines that includes altering the chromosomal promoter for the dam gene so as to alter Dam expression. Still another embodiment of the present invention for the preparation of live attenuated bacterial vaccines includes the mutation of the dam gene so as to alter the expression of Dam in the pathogenic bacteria.

BRIEF DESCRIPTION OF THE DRAWINGS

FIG. 1 shows differential digest results of *P. multocida* and *M. haemolytica*. Lane 1 shows *M. haemolytica* digested with Mbo I. Lane 2 shows, *M. haemolytica* digested with Dpn I. Lane 3 shows *M. haemolytica* digested with Sau3A I. Lane 4 shows *P. nultocida* digested with Mbo I. Lane 5 shows *P. multocida* digested with Dpn I. Lane 7 shows *P. multocida* digested with Sau3A I.

FIG. 2 shows differential digests results of DG105, DG98, DG105/pCLPm2, and DG105/pCLPm3. Lane 1 shows DG105 digested with Mbo I. Lane 2 shows DG105 digested with Dpn I. Lane 3 shows DG105 digested with Sau3A I. Lane 4 shows DG98 digested with Mbo I. Lane 5 shows DG98 digested with Dpn I. Lane 6 shows DG98 digested with Sau 3 A I. Lane 7 shows DG 105/pCLPm3 digested with Mbo I. Lane 8 shows DG105/pCLPm3 digested with Dpn I. Lane 9 shows DG105/pCLPm3 digested with Sau3A I. Lane 10 shows DG105/pCLPm2 digested with Mbo I. Lane 11 shows DG105/pCLPm2 digested with Sau3A I. Lane 12 shows DG105/pCLPm2 digested with Sau3A I.

DETAILED DESCRIPTION

The specific embodiment of the present invention described herein and shown in FIGS. 1-2 is a non-limiting example of the inventors' discovery of novel attenuated live bacteria vaccines and methods of producing the same. The detailed description of the method of vaccine preparation provided below includes the exemplary processes employed to produce attenuated live bacteria vaccines of the Pasteurellaceae family. It is within the concept of the present invention to produce vaccines for a wide variety of bacterial pathogens using any of the methods disclosed herein. The invention is limited only by the claims of the present application.

The following exemplary embodiments of the present invention involve the alteration of DNA adenine methylase (Dam) expression in veterinary pathogenic bacteria. The inventors have discovered that altered Dam expression in veterinary pathogens causes them to be attenuated in their natural host(s) and to be effective as live, attenuated vaccines. Of particular interest are such vaccines developed for the Pasterurellaceae family; to include, *Pasteurella multocida, Mannheimia haemolytica, Actinobacillus pleuropneumoniae, Haemophilus somnus, Actinobacillus suis*, and *Haemophilus parasuis*; although it is within the concept of the present invention to apply the discovery of the present invention and the methods disclosed herein to the production of a wide variety of bacterial vaccines.

As shown in the first non-limiting example provided below, the inventors discovered that an effective live vaccine can be obtained when a copy of the dam gene from one of the pathogens listed above is cloned into a plasmid capable of replication in the same Pasteurellaceae species such that it is overexpressed from either a lac promoter, tac promoter, araBAD promoter, trc promoter, trp promoter, T7, SP6, or T5 bacteriophage promoters, a native promoter from that species, or other appropriate promoter. The plasmid containing the Pasteurellaceae dam gene is then transferred into the pathogens to cause increased expression of Dam and results in the formation of a live attenuated bacterial vaccines. To ensure plasmid stability, a mutation is created in a gene located in the chromosome of the bacteria carrying the plasmid such that said bacteria cannot survive under certain conditions, and an intact copy of this mutated gene is expressed from the same plasmid carrying the Pasteurellaceae dam gene. This mutation can be made in any gene essential for survival of the bacterial under certain conditions.

EXAMPLES

Bacterial strains and plasmids. A list of the bacterial strains and plasmids employed in this example of the concept of the present invention is shown in Table 1. Sources of the bacterial strain and plasmids are as shown in Table 1, with some being provided by the inventors from the study associated with this present application. *Escherichia coli* strains were grown at 37° C. on Luria-Bertani (LB) agar or broth. *Pasteurella multocida* and *Mannheimia haemolytica* strains were grown at 37° C. on brain heart infusion (BHI) agar or broth. For plasmid maintenance, antibiotics were added to the following final concentrations: ampicillin, 200 µg/ml; kanamycin, 50 µg/ml; and streptomycin, 80 µg/ml. Isopropyl 6-D-thiogalactopyranoside (IPTG) and 5-bromo-4-chloro-3-indolyl β-D-galactopyranoside (X-gal) were used at final concentrations of 80 µM and 70 µg/ml, respectively, for blue white screening on LB agar.

TABLE 1

Bacterial strains and plasmids

| | Description | Source |
|---|---|---|
| Bacterial strain | | |
| *Pasteurella multocida* 11039 | Wild type serotype A1 | ATCC |
| *Mannheimia haemolytica* D153 | Wild type | USDA National Animal Disease Center |
| *E. coli* XL1-Blue MRF' | Cloning strain contains an F' episome with lacI$^q$ Z ΔM15 for blue white screening | Stratagene |
| *E. coli* DG98 | Parent strain for DG105 | ATCC |
| *E. coli* DG105 | dam mutant (dam-13, lacI$^q$) | ATCC |
| Plasmid | | |
| pT7Blue | Commercial cloning vector | Novagen |
| pGEM-3Z | Commercial cloning vector | Promega |
| pBluescript SK- | Commercial cloning vector | Stratagene |
| pCLPm1 | pGEM-3Z with 1.4 kb *P. multocida* chromosomal EcoR I insert containing the 3' end of aroB and the first 672 bp of dam | This study |
| pCLPm2 | pT7Blue with 3.0 kb insert containing *P. multocida* dam; oriented so that dam is in opposite orientation from lacZ promoter | This study |
| pCLPm3 | pBluescript with same insert as pCLPm2; dam gene oriented so that it is expressed from lacZ promoter | This study |
| pLS88 | *E. coli* shuttle vector that replicates in *Pasteurellaceae* | 33 |
| pLSdam | pLS88 with pCLPm3 insert; lacZ promoter removed | This study |
| pLSdam2 | pLS88 with pCLPm3 insert; lacZ promoter intact | This study |

Detection of dam function in *P. multocida* and *M. haemolytica*. To determine whether *P. multocida* and *M. haemolytica* contain functional dam genes, the inventors used differential digestion with restriction endonucleases Sau3A I, Mbo I, and Dpn I[28]. First, genomic DNA was isolated from 100 ml cultures of *P. multocida* 11039 and *M. haemolytica* D153 by phenol/chloroform extraction followed by precipitation with isopropanol[29]. Genomic DNA was then digested with Sau3A I, Dpn I and Mbo I (New England BioLabs, Beverly, Mass. USA) and visualized by agarose gel electrophoresis.

Cloning the *P. multocida* A1 dam gene. A 459 bp fragment of the *P. multocida* A1 dam gene was amplified from strain 11039 chromosomal DNA using primers HAPdamP1 having nucleotide sequence GGGCGCTGGAGCAGTATT (SEQ ID NO. 1) and HAPdam M1 having nucleotide sequence TGTAGCGGAGCATAAGGT (SEQ ID NO. 2), which were designed from the *Haemophilus influenzas* dam sequence. Cycle conditions were at 95° C. for 30 seconds, 66° C. for 1 min, and 72° C. for 45 s for 35 cycles, with an initial denaturation step at 95° C. for 2 min and a final extension step at 72° C. for 10 min. The 459 bp amplicon was isolated from a 0.7% agarose gel and eluted using QIAQuick Gel Extraction Kit (Qiagen, Valencia, Calif. USA) and used as template for a second round of PCR using the same primers and conditions.

To clone the *P. multocida* EcoR I fragment containing the dam gene, EcoR I digested *P. multocida* chromosomal DNA was cloned into EcoR I digested pGEM-3Z. Following transformation of the ligation into XL1-Blue MRF' by electroporation, white colonies were screened by colony hybridization using the 459 bp dam amplicon as a probe. Plasmid DNA from a positive clone was isolated and found to contain a 1.4 kb insert; this plasmid was designated pCLPm1.

Initial sequencing of the pCLPm1 insert indicated that it did not contain the 3' end of the dam gene. Subsequent to this cloning step, the *P. multocida* A3 chromosomal sequence became available[20]; therefore, the A3 chromosomal sequence flanking the dam gene was analyzed for PCR primer suitability using Oligo version 5.0 (Molecular Biology Insights, Cacade, Colo. USA). Two oligonucleotide primers, Pm1219DamM having nucleotide sequence TGAG-GAAACGGTCTGGTTTCTC (SEQ ID NO. 3) and Pm1223DamP having nucleotide sequence GCTG-GAAAATTGCGTCTCGTC (SEQ ID NO. 4), were selected and synthesized by Sigma Genosys (The Woodlands, Tex. USA). Using *P. multocida* ATCC 11039 genomic DNA as the template, a 3 kilobase amplicon containing the *P. multocida* dam gene was amplified by PCR under the following cycling conditions: 95° C. for 30 seconds, 64° C. for 1 min, and 72° C. for 2 min for 35 cycles, with an initial denaturation step at 95° C. for 2 min and a final extension step at 72° C. for 10 min.

The 3 kb *P. multocida* PCR fragment containing the dam gene was ligated into pT7Blue (Novagen, Madison, Wis. USA) by blunt end ligation using the Perfectly Blunt Cloning Kit (Novagen), followed by transformation into NovaBlue Singles Competent Cells (Novagen). Plasmid DNA was isolated from white colonies using the QIAprep spin miniprep kit (Qiagen), and one clone with the predicted insert size was selected and designated pCLPm2.

Sequence determination, assembly, and analysis. To determine the complete sequence of the *P. multocida* A1 dam gene, portions of the pCLPm1 and pCLPm2 inserts were sequenced on both strands using the Applied Biosystems Dye Terminator Cycle Sequencing Ready Reaction Kit protocol for sequencing double stranded plasmid DNA. Primers Universal and T7 were used for the initial sequencing reactions, and subsequent reactions used custom oligonucleotide primers (Sigma Genosys). Sequencing reactions were resolved on an Applied Biosystems Prism 310 Genetic Analyzer. Sequence results were assembled using SeqMan v5.0 (DNAStar, Madison, Wis.) and compared with published dam gene sequences using BLAST[30]. Percent identities were determined using the CLUSTAL W method[31] with MegAlign v5.0 (DNAStar). Prokaryotic promoters were predicted with the assistance of Neural Network Promoter Prediction[32]. The final sequence of the *P. multocida* A1 dam gene was deposited in GenBank (accession AF411317).

Expression of the *P. multocida* A1 dam gene from a lacZ promoter. To orient the *P. multocida* dam gene downstream of a lacZ promoter, the insert from pCLPm2 was subcloned into pBluescript. Using pCLPm2 DNA as template, a 3 kilobase fragment containing the *P. multocida* dam gene was amplified by PCR using AmpliTaq DNA polymerase (Perkin Elmer, Boston, Mass. USA) with primers 17 and U19. Optimal PCR conditions were the same as previously described for amplification of the 3 kb *P. multocida* dam fragment, except the annealing temperature was changed to 57° C. for 1 min per cycle. The 3 kb band was excised from a 0.7% agarose gel, and DNA was eluted using the Qiaquick gel extraction kit. The ends of the 3 kb fragment were digested with BainH I and Sal I and ligated into pBluescript. One clone with the predicted insert size was selected and designated pCLPm3. One end of the insert was sequenced to confirm correct orientation of the dam gene in relation to the lacZ promoter using the T3 primer.

Complementation of an *E. coli* dam mutant. Plasmids pCLPm2 and pCLPm3 were transferred into *E. coli* dam mutant strain DG105 by electroporation[29]. To assess dam function in the resulting strains, genomic DNA from DG105, DG105 with pCLPm2, DG105 with pCLPm3, and *E. coli* parent strain DG98 was isolated, digested with Sau3A I, Dpn I and Mbo I, and analyzed by 0.5% agarose gel electrophoresis.

Effect of *P. multocida* dam expression on spontaneous mutation frequency in *E. coli*. Overexpression of the native *E. coli* dam gene in *E. coli* causes an increased spontaneous mutation frequency. To determine whether overexpression of the *P. multocida* dam gene has the same effect in *E. coli*, the inventors compared the spontaneous mutation frequencies of dam mutant DG105, parent strain DG98, DG105 with pCLPM2, and DG105 with pCLPm3. The spontaneous development of resistance to rifampin was used to measure mutability of the strains. Briefly, 5 ml cultures of each strain were started from single colonies, incubated for 18 h, and aliquots (0.1 ml) of the diluted suspensions were spread in triplicate on BHI plates with 100 µg/ml of rifampin. The cultures were also serially diluted in phosphate buffered saline (PBS), and viable bacterial counts were determined by spreading diluted bacterial suspensions on BHI plates without antibiotics.

Mutation rates for each strain were determined by dividing the number of rifampin-resistant mutants by the total viable bacterial counts. Four independent replicates of the experiment were run from separate bacterial cultures, and the average mutation rates of the strains were compared by analysis of variance (ANOVA) for a randomized complete block design with run as the blocking factor. If significant differences among strains were found at the 5% level of significance, means were separated using the least significant difference test and 95% confidence intervals were calculated to characterize the biological importance of those differences. The homogeneity of variances and normality assumptions necessary for valid application of ANOVA were examined by Levene's test and by stem-and-leaf and normal probability plots, respectively. Statistical computations were performed using the SAS System for Windows, Version 8 (SAS Institute Inc., Cary, N.C.).

Effect of dam overexpression in *P. multocida*. To overexpress the *P. multocida* dam gene in strain 11039, the insert from pCLPm3 was transferred into pLS88, a shuttle vector that replicates both in *E. coli* and in the Pasteurellaceae [33]. Two pLS88 derivatives were constructed from pCLPm3: pLSdam, which has the *P. multocida* dam gene expressed from its native promoter, and pLSdam2, which has the *P. multocida* dam gene expressed from the lacZ promoter.

To construct pLSdam, a 1.7 kb fragment was amplified from pCLPm3 by PCR using primers T7P1 having nucleotide sequence GGATCCTGCGTTATCCCC (SEQ ID NO. 5) and CLdamM20 having nucleotide sequence TCTAGATGT-TGCCAATGC (SEQ ID NO. 6). Cycle conditions were at 95° C. for 30 seconds, 67.5° C. for 1 min, and 72° C. for 30 s for 35 cycles, with an initial denaturation step at 95° C. for 2 min and a final extension step at 72° C. for 10 min. The 1.7 kb amplicon was digested with BainH I and Xba I, which removed the lacZ promoter, and ligated into BamHI and Xba-digested pLS88.

To construct pLSdam2, pCLPm3 was digested with Afl III and HinD III, followed by treatment with the Klenow fragment of DNA polymerase I to create blunt ends. The resulting 1.6 kb fragment from pCLPm3 retained the *P. multocida* dam gene downstream of the lacZ promoter. The 1.6 kb fragment was excised from a 0.7% agarose gel, eluted using the Qiaquick gel extraction kit, and ligated into EcoR V-digested pLS88.

Both pLSdam and pLSdam2 were transferred into *P. multocida* 11039 by electroporation using described conditions[34] with a BioRad Gene Pulser II. Spontaneous mutation frequencies were determined for wild type strain 11039, 11039 with pLSdam, and 11039 with pLSdam2 by measuring the development of rifampin resistance using the method described above for *E. coli* strains. Five individual replicates were run for each strain: 11039, 11039/pLSdam, and 11039/pLSdam2.

Mouse virulence assay. The virulence of 11039/pLSdam2 was compared to 11039 using a mouse model with five mice per treatment. Female 6-8 week old BALB/cJ mice were obtained from the Jackson Laboratory (Bar Harbor, Me. USA), randomly divided into nine cages, and allowed to acclimate for one week. Bacterial broth cultures (11039 and 11039/pLSdam2) were incubated for 18 h and serially diluted in normal saline solution. Mice were injected intraperitoneally with 0.1 ml of an appropriate dose of either 11039 or 11039/pLSdam2. Four treatments were challenged with varying doses of 11039, four were challenged with 11039/pLSdam2, and one treatment was sham exposed to PBS. Mice were monitored for seven days, and mice surviving at the end of the challenge were euthanized.

Results

Figure 1:
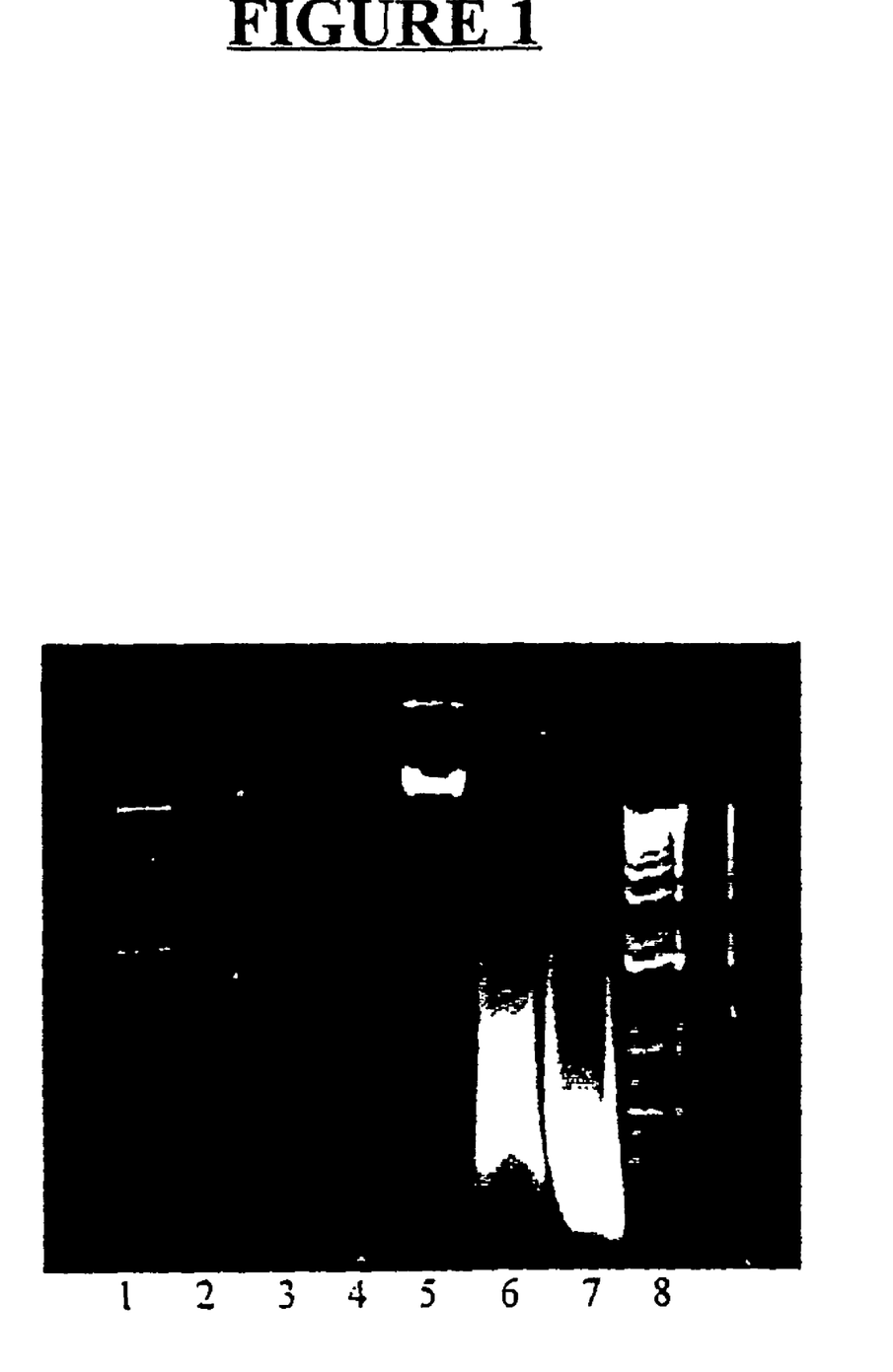

Phenotypic detection of Dam function in *P. multocida* and *M. haemolytica*. Sau3A I, Dpn L and Mbo I all recognize and cleave GATC sequences. However, Dpn I only cleaves GATC sites whose adenine residue has been methylated, while Mbo I only cleaves umnethylated GATC sites. Sau3A I cleaves GATC sites regardless of methylation state. Therefore, differential digestion of bacterial genomic DNA with Sau3A I, Dpn I, and Mbo I can be used to detect Dam activity. Our results indicated that both *P. multocida* strain 11039 and *M. haemolytica* strain D153 have functional Dam activity (See FIG. 1).

*P. multocida* A1 dam gene sequence results. The *P. multocida* A1 dam sequence was found to be 99.4% identical to the published *P. multocida* A3 dam sequence (5 nucleotide differences). The deduced amino acid sequences of the *P. multocida* A1 and A3 Dam proteins were 100% identical.

As expected, the *P. multocida* dam gene had higher sequence identity with the *H. influenzae* dam gene than with the other reported bacterial dam gene sequences (Table 2). Among gram-negative species, the dam gene is well conserved across four families, with identities ranging between 50-60%. The *P. multocida* dam gene was the largest of the known dam gene sequences (Table 2). By CLUSTAL W alignment, the additional coding sequence for the *P. multocida* dam gene was located at the 5' end of the gene, with an extra 39 bp at the 5' end of the gene compared to *H. influenzae* dam and an extra 72 bp at the 5' end compared to dam sequences from other species.

TABLE 2

DNA adenine methylase gene comparisons between
*P. multocida* and other gram-negative species

| Species | Size (nucleotides) | Nucleotide identity | Amino acid identity | Accession |
|---|---|---|---|---|
| *Pasteurella multocida* | 903 | — | — | AF411317 |
| *Haemophilus influenzas* | 861 | 68.9 | 68.2 | U32705 |
| *Escherichia coli* | 837 | 58.2 | 55.4 | V00272 |
| *Salmonella enterica* | 837 | 58.5 | 55.0 | AE008860 |
| *Serratia marcescens* | 813 | 57.4 | 51.9 | X78412 |
| *Yersinia pseudotuberculosis* | 816 | 52.1 | 51.3 | AF274318 |
| *Vibrio cholerae* | 834 | 60.0 | 56.7 | AF274317 |
| *Neisseria meningitidis* | 816 | 57.2 | 47.2 | AF091142 |

The *E. coli* dam gene is part of a superoperon that includes several genes under complex regulatory control[35]. Immediately upstream of *E. coli* dam is urf, which is preceded by aroB and aroK. A 90 bp gap is between arob and urf, and a 100 bp gap is between aroK and urf. The aroK and aroB products function in aromatic amino acid biosynthesis, while urf and dam are involved in cell cycle regulation. No promoter activity is located immediately of *E. coli* dam, but a weak promoter is located upstream of urf within the aroB sequence[35]. Another strong promoter is located upstream of aroB.

By contrast, aroB in *P. multocida* is located immediately upstream of dam with only a 4 bp gap between the genes, which is similar to the arrangement in *H. influenzas*. Our promoter analysis detected a potential promoter upstream of *P. multocida* dam within the aroB coding sequence. The 5' end of this promoter was located 115 bp upstream of the *P. multocida* dam start codon and had the sequence TGGAAA-17 bp-TAGCGT-5 bp-G (SEQ ID NO: 7).

Figure 2:
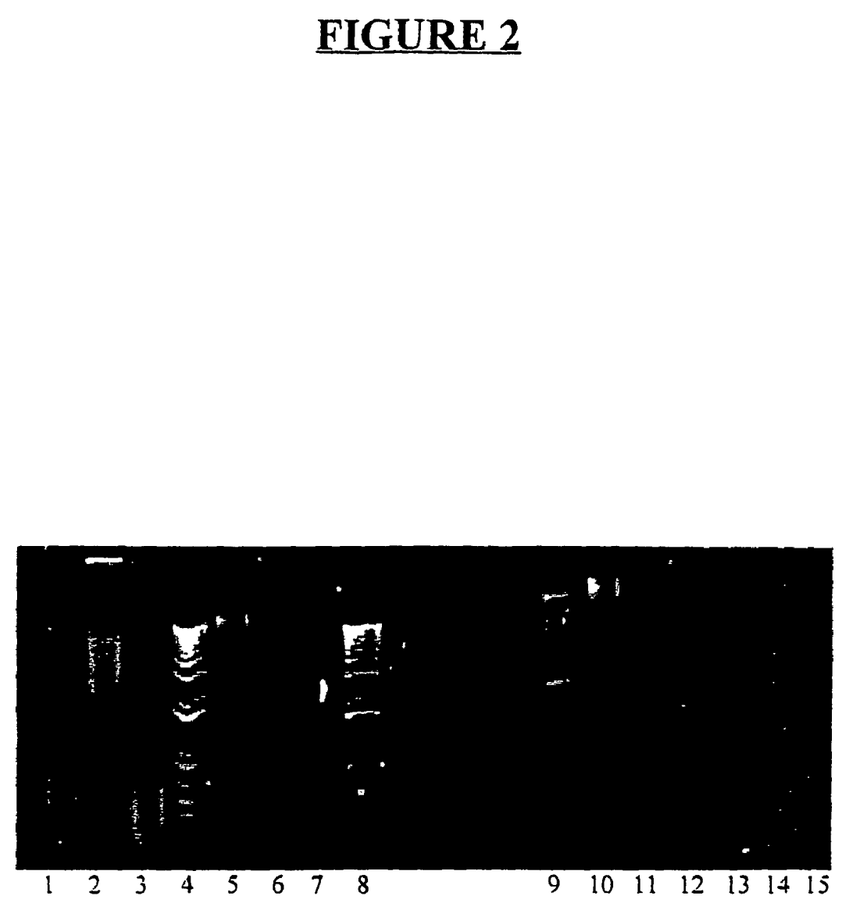

Complementation of an *E. coli* dam mutant. As described above in Methods, pCLPm2 contains the *P. multocida* dam gene cloned in the opposite orientation of the lacZ promoter in pT7Blue, while pCLPm3 contains the *P. multocida* dam gene oriented downstream of the lacZ promoter in pBluescript. When they were transferred into *E. coli* dam mutant strain DG105, both plasmids were able to restore Dam function (See FIG. 2). The pCLPm2 insert contained only 117 bp of native *P. multocida* chromosomal sequence upstream of the dam start codon; this indicated that the potential promoter identified within the 115 bp upstream of the *P. multocida* dam gene is functional.

Effect of *P. multocida* dam expression on spontaneous mutation frequency in *E. coli*. As expected, the spontaneous mutation frequency of *E. coli* dam mutant DG105 was significantly higher than the mutation rate of the parent wild type strain DG98 (Table 3). The mutation rate of DG105/pCLPm2 was also significantly higher than wild type, and although the mutation rate of DG105/pCLPm3 was not significantly higher than wild type, it was similar to the mutation rate for DG105/pCLPm2. DG105 had a higher mutation rate than both DG105/pCLPm2 and DG105/pCLPm3, although the difference was not statistically significant.

TABLE 3

Spontaneous mutation frequency in *E. coli* strains
DG98, DG105, DG105/pCLPm2, and DG105/pCLPm3

| Strain | Mutation rate* | Ratio† |
|---|---|---|
| DG98 | $0.24 \pm 0.06^a$ | |
| DG105 | $7.43 \pm 3.18^b$ | 30.7 |
| DG105/pCLPm2 | $4.85 \pm 3.08^b$ | 20.1 |
| DG105/pCLPm3 | $4.33 \pm 2.28^{ab}$ | 17.9 |

*Number of mutants per $10^7$ CFU
†Ratio of mutation rate for the indicated strain divided by the mutation rate for DG98.

The increased mutation rates of DG105/pCLPm2 and DG105/pCLPm3 compared to wild type indicates that overexpression of the *P. multocida* dam gene causes increased spontaneous frequency in *E. coli*. Increased mutation frequency has already been demonstrated in *E. coli* overexpressing an *E. coli* dam gene[36]. The mutation rates of DG105/pCLPm2 and DG105/pCLPm3 were similar; apparently the native dam promoter in pCLPm2 was just as effective in expressing dam in *E. coli* as the lacZ promoter.

Effect of dam overexpression in *P. multocida*. Plasmid pLSdam is similar to pCLPm2 in that the insert contains the *P. multocida* dam gene under the control of its native promoter, while pLSdam2 is similar to pCLPm3 in that dam is expressed from a lac promoter. Both plasmids were transferred into *P. multocida* 11039 to determine whether the native dam promoter would be as effective in causing overexpression in *P. multocida* as it was in *E. coli*.

Surprisingly, transfer of pLSdam actually lowered the spontaneous mutation rate of strain 11039 compared to the wild type strain, although the difference was not statistically significant (Table 4). However, 11039/pLSdam2 had a significantly higher spontaneous mutation rate compared to 11039, demonstrating that this strain had increased Dam activity and that the lac promoter was effective in causing dam overexpression in *P. multocida*.

TABLE 4

Spontaneous mutation frequency in *P. multocida*
strain 11039, 11039/pLSdam, and 11039/pLSdam2

| Strain | Mutation rate* | Ratio† |
|---|---|---|
| 11039 | $0.30^a$ | |
| 11039/pLSdam | $0.14^a$ | 0.47 |
| 11039/pLSdam2 | $2.37^b$ | 7.9 |

*Number of mutants per $10^7$ CFU
†Ratio of mutation rate for the indicated strain divided by the mutation rate for 11039.

Mouse virulence assay. A mouse virulence trial indicated that 11039/pLSdam retained full virulence compared to 11039, which was expected because the mutation rates of 11039 and 11039/pLSdam were not significantly different. However, a virulence assay with 11039/pLSdam2 demonstrated that this strain was clearly attenuated in mice compared to wild type strain 11039. Mice exposed to wild type strain 11039 were injected with 11 CFU/mouse, 23 CFU/mouse, 113 CFU/mouse, and 227 CFU/mouse; all four doses had 100% mortality. Mice exposed to 11039/pLSdam2 were injected with 17 CFU/mouse, 86 CFU/mouse, 171 CFU/mouse, and 856 CFU/mouse; all four doses had 0% mortality. Sham control mice also had 0% mortality.

Discussion

The inventors have demonstrated the function of DNA adenine methylase from *P. multocida*, which is an important etiologic agent of BRD in cattle. In other bacterial species, Dam is important in regulating and coordinating several cell functions, including initiation of chromosome replication, DNA repair, and gene transcription. As a result of its role in DNA repair, bacteria with altered Dam activity have increased mutability. Its role in regulation of gene transcription, particularly genes involved in pathogenicity, causes strains with altered Dam activity to be attenuated. The inventors compared *P. multocida* Dam function to Dam proteins from other bacterial species by measuring the effects of altered Dam activity on these two phenotypes: spontaneous mutation frequency and virulence in a mouse model.

*E. coli* dam mutants have an increased rate of spontaneous mutations, increased sensitivity to ultraviolet radiation and to base analogues such as 2-aminopurine (2-AP), and inviability when combined with a recA, recB, or recC mutation[37-39]. Dam methylates DNA at the $N^6$ position of adenine within GATC recognition sequences[40], which allows the methyl-directed mismatch repair system to distinguish between the template and nascent strands to correct misincorporated bases during DNA replication[37,41]. Interestingly, overproduction of Dam also increases mutability because methylation of the daughter strand occurs too quickly, which also prevents the mismatch repair system from distinguishing between the template and daughter strands[36,42].

*P. multocida* Dam has 55% identity with *E. coli* Dam, and the inventors demonstrated that it is able to complement an *E. coli* dam mutant. In addition, overproduction of *P. multocida* Dam in *E. coli* caused an approximate 20-fold increase in the spontaneous mutation frequency. This result is similar to the effect of increased native Dam activity in *E. coli*; a mutant with 50-fold increase in Dam activity had a corresponding 30-fold increase in development of spontaneous rifampin resistance[36].

The potential native dam promoter sequence identified on pCLPm2 (located within the aroB coding sequence) appeared relatively weak, having 5/12 mismatches compared to the *E. coli* consensus promoter. In *E. coli*, the promoter upstream of dam and urf located within the aroB coding sequence is also relatively weak, having 3- to 4-times less activity than another promoter located upstream of aroB[35]. Therefore, it was surprising that the spontaneous mutation frequency in DG105/pCLPm2 was similar to that of DG105/pCLPm3 because it was expected the lac promoter in pCLPm3 would cause increased Dam activity compared to the pCLPm2 construct with a concurrent increase in mutation frequency.

By comparison, when the *P. multocida* dam gene was expressed from its native promoter in strain 11039 using shuttle vector pLS88 (pLSdam), there was no significant increase in spontaneous mutation frequency. On the other hand, expression of *P. multocida* dam from a lacZ promoter in 11039 (pLSdam2) did cause increased spontaneous mutation frequency. One possible explanation for the different effects of the native dam promoter on spontaneous mutation frequency in *E. coli* and *P. multocida* is that the high copy number of pT7Blue, a pUC derivative, may be the cause of increased Dam production in *E. coli*. pLS88 is not likely to have as high copy numbers in *P. multocida*. Alternatively, dam expression from the native promoter may be subject to transcriptional regulation in *P. multocida*, and the transcriptional regulator that controls dam expression may not be present in *E. coli*, resulting in unrestricted expression.

Dam overproducing strains of *Salmonella enterica, Yersinia pseudotuberculosis,* and *Vibrio cholerae* are all attenuated[25,35]. Similarly, our Dam overproducing *P. multocida* strain was attenuated using a mouse model. The attenuation of strains with altered dam expression is apparently due to "inappropriate" expression of virulence factors that results from the failure of Dam to regulate their transcription[25]. In *Salmonella*, a similar attenuating effect occurs in dam deletion mutants[25]; mutation of the dam gene is lethal in *Y. pseudotuberculosis* and *V. cholerae*[26].

Interestingly, the inappropriate expression of virulence factors in Dam altered strains not only causes attenuation, but it also renders them highly effective as live attenuated vaccines[25,26,43]. Although *P. multocida* immunogens have been identified that have potential as vaccines[44,45], there is still a need for an effective *P. multocida* BRD vaccine. Killed bacterins have had little effect in preventing BRD[46]; however, live vaccines have demonstrated efficacy[46-48].

In the non-limiting example described above, the inventors have demonstrated that alteration of dam expression in *P. multocida* can enable the development of a live attenuated vaccine. It is entirely within the concept of the present invention to provide novel attenuated live bacteria vaccines for a wide range of other pathogens, which can include, for example, bacteria selected from the group including *Salmonella, E. Coli, Haemophilus, Streptococcus, Helicobacter, Shigella, Bibrio, Treponeina, Yersinia, Neisseria, Porphyronionas, Legionella, Actinobacillus, Pasteurella, Mannheimia*, and the like.

In addition to the detailed discussion of a first embodiment of the present invention, alternative embodiments of the present invention include methods of altering Dam expression to obtain effective life vaccines by 1) altering the chromosomal promoter for the dam gene so as to alter Dam expression or 2) mutation of the dam gene so as to alter the expression of Dam in any of the above listed pathogenic bacteria. The bacteria having the altered chromosomal promoter for the dam gene or having a mutated dam gene then fails to properly express Dam and is rendered non-pathogenic and by altering Dam expression the bacteria is attenuated and is suitable for use in live attenuated bacterial vaccines.

In the first alternative embodiment, the promoter for the native dam gene in the chromosome of one of the pathogens of the Pasteurellaceae family is replaced with a promoter that would cause increased Dam expression in the bacteria so as to render it non-pathogenic. It is also within the scope of the invention, that in this first alternative embodiment, the replacement promoter would cause decreased Dam expression in the bacteria, which would also serve to render the bacterial non-pathogenic and suitable for use as an attenuated live bacteria vaccine. Acceptable methods for the replacement of the promoter would be known and understood by one of ordinary skill in the art.

In a second alternative embodiment, the native dam gene in one of the pathogens of the Pasteurellaceae family is mutated. The mutation can be achieved either by using the cloned native dam gene from the pathogen to mutate the chromosomal copy of the dam gene by homologous recombination, or by transposon mutagenesis, or by site-directed mutagensis.

Dam activity may be increased or decreased, and Dam activity may be altered on any level, including transcription and/or translation. With respect to translation, for example, activity can be altered in any number of ways, including the amount of protein produced and/or that nature (i.e., structure) of the protein produced. For example, a mutation could result in increasing or reducing the amount of Dam produced by the cell (due to affecting transcriptional and/or post-transcriptional events); alternatively, a mutation could give rise to an altered Dam with altered activity. Generating mutations and mutants which alter Dam activity use techniques, are well known in the art. For example in the first alternative embodiment of the present invention, Dam production can be increased or lowered by using a promoter which is known to initiate transcription at a higher or lower level. Assays to determine level of transcription from a given transcriptional regulatory element such as a promoter are well known in the art.

In the second alternative embodiment of the present invention, a different dam gene could be used that is known to produce higher or lower levels of Dam than is found in the wild type bacteria without departing from the scope of the inventor's discovery. Mutations can be made within the dam gene itself (including transcriptional and/or translational regulatory elements) as well as a gene or genes which affect Dam production and/or activity.

By one embodiment of the present invention, pathogenic bacteria are made attenuated, preferably avirulent, as a result of a non-reverting mutation that is created in at least one gene, which thereby alters the expression of Dam. The regulation of genes by Dam is sensitive to Dam concentrations; therefore, over-expression of Dam as well as under-expression of Dam results in the attenuation of the pathogen. In the second embodiment of the present invention, the mutation is preferably made in the dam gene itself, however, it is within the concept of the present invention that the vaccines according to the present invention may be produced by mutating a related gene or genes either upstream or downstream of the dam gene, whose expressed product activates or represses the dam gene or, in the alternative, a mutation is constructed in at least one virulence gene that is regulated by Dam.

While a single non-reverting mutation provides a high degree of security against possible reversion to virulence, it is within scope of the invention to provide additional security in a second separate and unrelated mutation.

Further, while the present invention has been described with reference to specific embodients and exemplary bacteria species, it will be understood by those skilled in the art that a variety of changes may be made and the substitution of equivalents may be made without departing from the true spirit and scope of the present invention. Many modifications may be made to adapt a particular situation or a particular selected pathogen to the inclusive concept of the present invention. All such modifications or adaptations are intended to be within the scope of the claims appended hereto.

The complete disclosure of all references cited in this application are fully incorporated herein by reference.

References

1. Carter G. Observations on the pathology and bacteriology of shipping fever in Canada. *Can J Comp Med* 1954; 18:359-64.

2. Collier J. Pasteurellae in bovine respiratory disease. *J Am Vet Med Assoc* 1969; 140:807-10.

3. Scheifer B, Ward G E, Moffatt R E. Correlation of microbiological and histological findings in bovine fibrinous pneumonia. *Vet Pathol* 1978; 15:313-321.

4. Purdy C W, Raleigh R H, Collins J K, et al. Serotyping and enzyme characterization of *Pasteurella haemolytica* and *Pasteurella multocida* isolates recovered from pneumonic lungs of stressed feeder calves. *Curr Microbiol* 1997; 34:244-9.

5. Allen J W, Viel L, Bateman K G, et al. The microbial flora of the respiratory tract in feedlot calves: associations between nasopharyngeal and bronchoalveolar lavage cultures. *Can J Vet Res* 1991; 55:341-6.

6. Singer R S, Case J T, Carpenter T E, et al. Assessment of spatial and temporal clustering of ampicillin- and tetracycline-resistant strains of *Pasteurella multocida* and *P. haemolytica* isolated from cattle in California. *J Am Vet Med Assoc* 1998; 212:1001-5.

7. Gourlay R N, Thomas L H, Wyld S G. Experimental *Pasteurella multocida* pneumonia in calves. *Res Vet Sci* 1989; 47:185-9.

8. Bryson D G, McFerran J B, Ball H J, et al. Observations on outbreaks of respiratory disease in housed calves—(1) Epidemiological, clinical and microbiological findings. *Vet Rec* 1978; 103:485-9.

9. Virtala A M, Mechor G D, Grohn Y T, et al. Epidemiologic and pathologic characteristics of respiratory tract disease in dairy heifers during the first three months of life. *J Am Vet Med Assoc* 1996; 208:2035-42.

10. Boyce J D, Adler B. The capsule is a virulence determinant in the pathogenesis of *Pasteurella multocida* M1404 (B:2). *Infect Immun* 2000; 68:3463-8.

11. Rimler R B, Rebers P A, Phillips M. Lipopolysaccharides of the Heddleston serotypes of *Pasteurella multocida*. *Am J Vet Res* 1984; 45:759-63.

12. Brogden K A, Rimler R B, Cutlip R C, et al. Incubation of *Pasteurella haemolytica* and *Pasteurella multocida* lipopolysaccharide with sheep lung surfactant. *Am J Vet Res* 1986; 47:727-9.

13. Confer A W, Suckow M A, Miloscio L, et al. Intranasal vaccination of rabbits with *Pasteurella multocida* a:3 OMPs and IROMPs. Proc. Conf Res Workers Anim Dis 80th Ann Mtg. 1999.

14. Geschwend G, Feist H, Erler W. [Investigation of outer membrane proteins of *Pasteurella*. 2: Iron-regulated outer membrane proteins of *Pasteurella multocida* and *Pasteurella haemolytica*]. *Berl Munch Tierarztl Wochenschr* 1997; 110:386-90.

15. Negrete-Abascal E, Tenorio V R, de la Garza M. Secretion of proteases from *Pasteurella multocida* isolates. *Curr Microbiol* 1999; 38:64-7.

16. Straus D C, Purdy C W, Loan R W, et al. In vivo production of neuraminidase by *Pasteurella haemolytica* in market stressed cattle after natural infection. *Curr Microbiol* 1998; 37:240-4.

17. White D J, Jolley W L, Purdy C W, et al. Extracellular neuraminidase production by a *Pasteurella multocida* A:3 strain associated with bovine pneumonia *Infect Immun* 1995; 63:1703-9.

18. Galdiero M, Palomba E, De L, et al. Effects of the major *Pasteurella multocida* porin on bovine neutrophils. *Am J Vet Res* 1998; 59:1270-4.

19. Fuller T E, Kennedy M J, Lowery D E. Identification of *Pasteurella multocida* virulence genes in a septicemic mouse model using signature-tagged mutagenesis. *Microb Pathog* 2000; 29:25-38.

20. May B J, Zhang Q, Li L L, et al. Complete genomic sequence of *Pasteurella multocida*, Pm70. *Proc Natl Acad Sci USA* 2001; 98:3460-5.

21. Blyn L B, Braaten B A, Low D A. Regulation of pap pilin phase variation by a mechanism involving differential dam methylation states. *Embo J* 1990; 9:4045-54.

22. Braaten B A, Nou X, Kaltenbach L S, et al. Methylation patterns in pap regulatory DNA control pyelonephritis-associated pili phase variation in *E. coli*. *Cell* 1994; 76:577-88.

23. van der Woude M W, Low D A. Leucine-responsive regulatory protein and deoxyadenosine methylase control the phase variation and expression of the sfa and daa pili operons in *Escherichia coli*. *Mol Microbiol* 1994; 11:605-18.

24. Henderson I R, Owen P. The major phase-variable outer membrane protein of *Escherichia coli* structurally resembles the immunoglobulin A1 protease class of exported protein and is regulated by a novel mechanism involving Dam and oxyR. *J Bacteriol* 1999; 181:2132-41.

25. Heithoff D M, Sinsheimer R L, Low D A, et al. An essential role for DNA adenine methylation in bacterial virulence. *Science* 1999; 284:967-70.

26. Julio S M, Heithoff D M, Provenzano D, et al. DNA adenine methylase is essential for viability and plays a role in the pathogenesis of *Yersinia pseudotuberculosis* and *Vibrio cholerae. Infect Immun* 2001; 69:7610-5.

27. Fleischmann R D, Adams M D, White O, et al. Whole-genome random sequencing and assembly of *Haemophilus influenzas* Rd. *Science* 1995; 269:496-512.

28. Palner B R, Marinus M G. The dam and dcm strains of *Escherichia coli*—a review. *Gene* 1994; 143:1-12.

29. Ausubel F M B R, Kingston R E, Moore D D, Seidman J G, Smith J A, Struhl K. Current Protocols in Molecular Biology. New York, N.Y.: John Wiley and Sons, 1994.

30. Altschul S F, Madden T L, Schaffer A A , et al. Gapped BLAST and PSI-BLAST: a new generation of protein database search programs. *Nucleic Acids Res* 1997; 25:3389-402.

31. Thompson J D, Higgins D G, Gibson T J. CLUSTAL W: improving the sensitivity of progressive multiple sequence alignment through sequence weighting, position-specific gap penalties and weight matrix choice. *Nucleic Acids Res* 1994; 22:4673-80.

32. Reese M G, Harris N L, Eeckman F H. Large scale sequencing specific neural networks for promoter and splice site recognition. Biocomputing: Proceedings of the 1996 Pacific Symposium 1996.

33. Willson P J, Albritton W L, Slaney L, et al. Characterization of a multiple antibiotic resistance plasmid from *Haemophilus ducreyi. Antimicrob Agents Chemother* 1989; 33:1627-30.

34. Jablonski L, Sriranganathan N, Boyle S M, et al. Conditions for transformation of *Pasteurella multocida* by electroporation. *Microb Pathog* 1992; 12:63-8.

35. Jonczyk P, Hines R, Smith D W. The *Escherichia coli* dam gene is expressed as a distal gene of a new operon. *Mol Gen Genet* 1989; 217:85-96.

36. Herman G E, Modrich P. *Escherichia coli* K-12 clones that overproduce dam methylase are hypermutable. *J Bacteriol* 1981; 145:644-6.

37. Glickman B, van den Elsen P, Radman M. Induced mutagenesis in dam-mutants of *Escherichia coli:* a role for 6-methyladenine residues in mutation avoidance. *Mol Gen Genet* 1978; 163:307-12.

38. Bale A, d'Alarcao M, Marinus M G. Characterization of DNA adenine methylation mutants of *Escherichia coli* K12. *Mutat Res* 1979; 59:157-65.

39. Marinus M G, Morris N R. Biological function for 6-methyladenine residues in the DNA of *Escherichia coli* K12. *J Mol Biol* 1974; 85:309-22.

40. Geier G E, Modrich P. Recognition sequence of the dam methylase of *Escherichia coli* K12 and mode of cleavage of Dpn I endonuclease. *J Biol Chem* 1979; 254:1408-13.

41. Modrich P. Methyl-directed DNA mismatch correction. *J Biol Chem* 1989; 264:6597-600.

42. Marinus M G, Poteete A, Arraj J A. Correlation of DNA adenine methylase activity with spontaneous mutability in *Escherichia coli* K-12. *Gene* 1984; 28:123-5.

43. Heithoff D M, Enioutina E Y, Daynes R A, et al. Salnonella DNA adenine methylase mutants confer cross-protective immunity. *Infect Immun* 2001; 69:6725-30.

44. Confer A W, Nutt S H, Dabo S M, et al. Antibody responses of cattle to outer membrane proteins of *Pasteurella multocida* A:3. *Am J Vet Res* 1996; 57:1453-7.

45. Adler B, Bulach D, Chung J, et al. Candidate vaccine antigens and genes in *Pasteurella multocida. J Biotechnol* 1999; 73:83-90.

46. Cardella M A, Adviento M A, Nervig R M. Vaccination studies against experimental bovine *Pasteurella pneumonia. Can J Vet Res* 1987; 51:204-11.

47. Panciera R J, Corstvet R E, Confer A W, et al. Bovine pneumonic pasteurellosis: effect of vaccination with live *Pasteurella* species. *Am J Vet Res* 1984; 45:2538-42.

48. Chengappa M M, McLaughlin B G, Kadel W L, et al. Efficacy of a live *Pasteurella multocida* vaccine for the prevention of experimentally induced bovine pneumonic pasteurellosis. *Vet Microbiol* 1989; 21:147-54.

---

What is claimed is:

1. An attenuated strain of a bacteria of the species *Mannheimia haemolytica*, said bacteria comprising altered DNA adenine methylase (Dam) activity such that the bacteria are attenuated.

2. The attenuated strain of claim 1, wherein the altered activity reduces Dam activity.

3. The attenuated strain of claim 2, wherein the altered activity eliminates Dam activity.

4. The attenuated strain of claim 1, wherein the altered activity is obtained by a deletion in a dam gene.

5. The attenuated strain of claim 1, wherein the altered activity is obtained by an increase in expression of Dam.

6. The attenuated strain of claim 1, wherein the altered activity is obtained by an artificially engineered change in a genome of a wild-type pathogenic bacteria.

7. The attenuated strain of claim 6, wherein the change in the bacteria's genome is a change selected from the group consisting of a deletion, an insertion and a mutation of the native sequence.

8. The attenuated strain of claim 1, wherein the altered activity is obtained by a heterologous nucleotide inserted into a wild-type pathogenic bacteria.

9. The attenuated strain of claim 8, wherein the heterologous nucleotide is operatively inserted into a plasmid and expresses DNA adenine methylase.

10. A composition comprising: a pharmaceutically acceptable excipient; and bacteria of the species *Mannheimia haemolytica* with altered DNA adenine methylase (Dam) activity which altered DNA adenine methylase activity renders the bacteria non-pathogenic.

11. The composition of claim 10, further comprising an adjuvant.

12. An immunogenic composition comprising: a pharmaceutically acceptable excipient; and live bacteria of the species *Mannheimia haemolytica* comprising altered DNA adenine methylase activity wherein the altered activity reduces virulence relative to the bacteria with wild-type Dam activity.

13. The immunogenic composition of claim 12, wherein the Dam activity is altered by a heterologous nucleotide.

14. The immunogenic composition of claim 12, wherein the Dam activity is altered by a mutation in the bacteria's genome which mutation alters a gene involved in expressing Dam in a manner selected from the group consisting of reduced expression, no expession, overexpression expression of a form of Dam altered from Dam native to the bacteria.

15. An attenuated strain of a bacteria of the species *Mannheimia Haemolytica*, said bacteria comprising a cloned dam gene capable of altered DNA adenine methylase (Dam) activity such that said bacteria are attenuated and suitable for use as a live vaccine.

16. The attenuated strain of claim 15, wherein said altered activity increases Dam expression.

17. The attenuated strain of claim 16, wherein said increased Dam expression is obtained by control of said cloned dam gene by a promoter.

18. The attenuated strain of claim 17, wherein said promoter is selected from the group consisting of a lac promoter, tac promoter, araBAD promoter, trc promoter, trp promoter, T7, SP6, or T5 bacteriophage promoters, a native promoter from that species, or other appropriate promoter.

19. A composition comprising: a pharmaceutically acceptable carrier in combination with a bacteria of the species *Mannheimia haemolytica* demonstrating altered DNA adenine methylase (Dam) activity, said altered activity being overexpression of Dam, whereby said overexpression of Dam renders the bacteria non-pathogenic and suitable as an attenuated live bacterial vaccine.

20. The composition of claim 19, wherein said over expression is obtained by control of said cloned dam gene by a promoter.

21. The composition of claim 20, wherein said promoter is selected from the group consisting of a lac promoter, tac promoter, araBAD promoter, trc promoter, trp promoter, T7, SP6, or T5 bacteriophage promoters, a native promoter from that species, or other appropriate promoter.

* * * * *